United States Patent
Xue et al.

(10) Patent No.: US 10,517,497 B2
(45) Date of Patent: Dec. 31, 2019

(54) SYSTEM AND METHOD FOR DETECTING ATRIAL FIBRILLATION

(71) Applicant: General Electric Company, Schenectady, NY (US)

(72) Inventors: Joel Xue, Wauwatosa, WI (US); Gordon Ian Rowlandson, Wauwatosa, WI (US); Robert Farrell, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 56 days.

(21) Appl. No.: 15/631,895

(22) Filed: Jun. 23, 2017

(65) Prior Publication Data

US 2018/0368715 A1    Dec. 27, 2018

(51) Int. Cl.
| A61B 5/04 | (2006.01) |
| A61B 5/046 | (2006.01) |
| A61B 5/00 | (2006.01) |

(52) U.S. Cl.
CPC .......... *A61B 5/04012* (2013.01); *A61B 5/046* (2013.01); *A61B 5/7221* (2013.01); *A61B 5/7264* (2013.01)

(58) Field of Classification Search
CPC ... A61B 5/04012; A61B 5/0452; A61B 5/046; A61B 5/0468
See application file for complete search history.

(56) References Cited

U.S. PATENT DOCUMENTS 5,456,261 A * 10/1995 Luczyk ................ A61B 5/0468
                                                                  600/509
6,490,479 B2    12/2002 Bock
7,702,382 B2    4/2010 Xue et al.
(Continued)

FOREIGN PATENT DOCUMENTS

WO    2011/061606 A2    5/2011
WO    2011/094227 A1    8/2011

OTHER PUBLICATIONS

GE Healthcare, "GE EK-Pro Arrhythmia Algorithm", DOC0783131, 2010 General Electric Company.
(Continued)

*Primary Examiner* — William J Levicky
(74) *Attorney, Agent, or Firm* — Andrus Intellectual Property Law, LLP

(57) ABSTRACT

A system for processing ECG to detect atrial fibrillation includes three software modules. A beat module is executable on a processor to receive a time series of ECG data, identify heart beats, and determine a beat AFIB value based on a timing of each identified heart beat. The beat AFIB value represents a presence or absence of AFIB based on variability in the timing of each identified heart beat. A segment module is executable to receive the time series of ECG data, divide the time series of ECG data into two or more time segments, and determine a segment AFIB value for each time segment. The segment AFIB value indicates a presence or absence of AFIB in the time segment based on whether any of a set of rhythms are identified. The AFIB detection module is executable to determine an AFIB identification value for each time segment based on the beat AFIB value during that time segment and the segment AFIB value for that time segment.

19 Claims, 4 Drawing Sheets

(56) References Cited

U.S. PATENT DOCUMENTS

| | | |
|---|---|---|
| 8,352,018 B2 | 1/2013 | Xue et al. |
| 2013/0041273 A1 | 2/2013 | Houben et al. |
| 2013/0303926 A1 | 11/2013 | Kurzweil et al. |
| 2016/0135706 A1 | 5/2016 | Sullivan et al. |

OTHER PUBLICATIONS

International Search Report and Written Opinion issued in connection with corresponding PCT Application No. PCT/US2018/038510 dated Oct. 19, 2018, 7 pages.

* cited by examiner

| Beat module (HMM output, 5 secs) | Beat AFIB value |
|---|---|
| Chaotic | 1 |
| Organized | 0 |
| Chaotic | 1 |
| Chaotic | 1 |
| Chaotic | 1 |
| ... | ... |

| Segment module (5 second output) | Segment AFIB value | Noise level |
|---|---|---|
| Afib | 1 | − |
| NSR | 0 | − |
| Afib | 0 | − |
| Afib | 0 | + |
| Afib | 1 | − |
| ... | ... | |

| AFIB detect module | | | |
|---|---|---|---|
| Hi-Sens | Bal. | Hi-Spec | CL % |
| 1 | 1 | 1 | CL |
| 0 | 0 | 0 | CL |
| 1 | 1 | 0 | CL |
| 1 | 1 | 0 | CL-20% |
| 1 | 1 | 1 | CL |
| ... | ... | ... | CL |

FIG. 2

SYSTEM AND METHOD FOR DETECTING ATRIAL FIBRILLATION

BACKGROUND

Atrial fibrillation ("AFIB") is the most common form of an irregular heartbeat. In AFIB, the heart's atrial walls do not produce an organized contraction and instead quiver. Thus, no organized heart beat rhythm can be detected from a patient experiencing AFIB. This arrhythmia puts patients at significant risk because it allows blood to pool and stagnate in the left atrium and, thus, form a clot. This clot can slough off and travel up to the brain where it can block sufficient blood flow to a portion of the brain where upon it will begin to die, thus causing a stroke. AFIB causes up to a quarter of all strokes and is often undetected until a stroke occurs. It is estimated that approximately a third of AFIB is asymptomatic. The prevalence of AFIB is high and age dependent, from 0.7% in the ages 55-59 to 17.8% for 85 years or older. Yet, AFIB is notoriously hard to detect.

The most common method for automatically detecting AFIB in ECG recordings relies heavily on the fact that AFIB is a chaotic atrial arrhythmia, randomly conducted to the ventricles. As such, the time periods between features of the QRS waves, as measured by the RR intervals, should be continuously varying in the presence of AFIB. It is this attribute of AFIB, that it is a continuously chaotic rhythm, that is used by most ambulatory ECG analysis programs to detect AFIB. However, RR intervals of normally conducted beats can vary for other types of benign arrhythmias that are not AFIB. Examples include premature atrial complexes (PACs) or sinus arrhythmia (SA), which are both quite common in the normal population. While these benign arrhythmias do exhibit as variability in RR intervals, these arrhythmias are not actually continuously chaotic or random.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a system for processing ECG to detect atrial fibrillation includes three software modules executable on a processor. A beat module is executable on the processor to receive a time series of ECG data, identify heart beats in the time series of ECG data, and determine a beat AFIB value based on a timing of each identified heart beat. The beat AFIB value represents a presence or absence of AFIB based on variability in the timing of each identified heart beat. A segment module is executable on the processor to receive the time series of ECG data, divide the time series of ECG data into two or more time segments, and determine a segment AFIB value for each time segment. The segment AFIB value indicates a presence or absence of AFIB in the time segment based on whether any of a set of rhythms are identified. The AFIB detection module is executable on the processor to determine an AFIB identification value for each time segment based on the beat AFIB value during that time segment and the segment AFIB value for that time segment.

One embodiment of a method of processing ECG data to detect atrial fibrillation includes receiving a time series of ECG data and identifying each heart beat within the time series of ECG data. A beat AFIB value is determined based on the timing of each identified heart beat, where the beat AFIB value represent a presence or absence of AFIB based on variability in each identified heart beat. The time series of ECG data is divided into two or more time segments, and a segment AFIB value is determined for each segment, wherein the segment AFIB value indicates a presence or absence in the time segment of ECG data based on whether any of a set of rhythms are identified. An AFIB identification value is then determined for each time segment based on the beat AFIB value during that time segment and the segment AFIB value for that time segment.

BRIEF DESCRIPTION OF THE DRAWINGS

The present disclosure is described with reference to the following Figures.

FIG. 2 provides tables depicting exemplary logic that may be utilized as part of a method of processing ECG data to detect atrial fibrillation according to the present disclosure.

DETAILED DESCRIPTION

Figure 1:
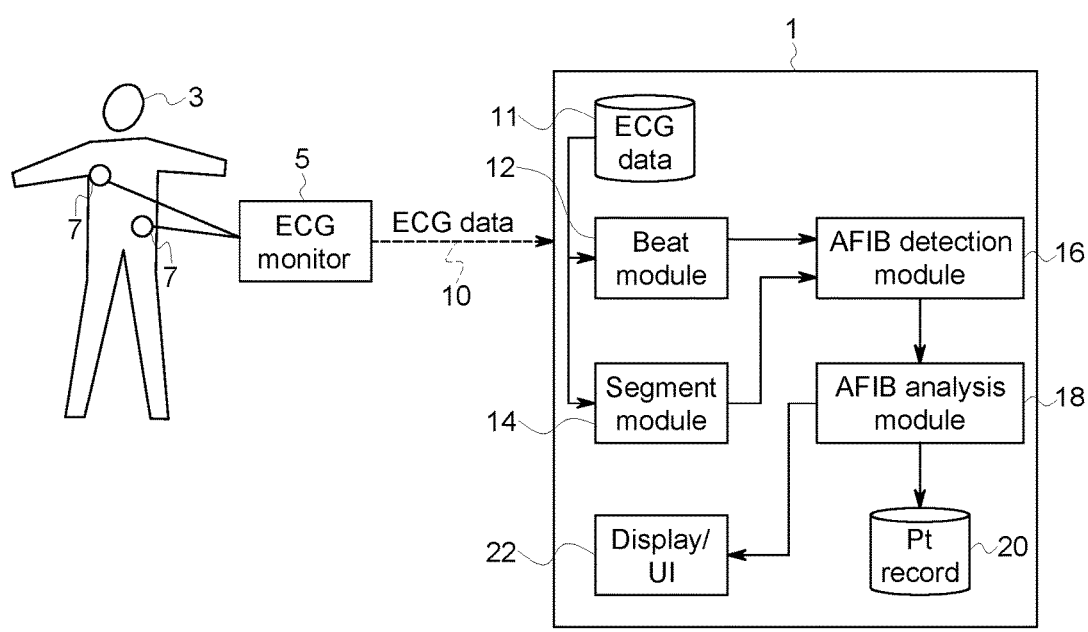
FIG. 1 schematically depicts one embodiment of a system for processing ECG data to detect atrial fibrillation.

Intermittent AFIB has been found to increase the risk of stroke, although perhaps to a lesser degree than persistent AFIB. Moreover, it has been found that a significant portion of those who suffer from transient ischemic attacks or cryptogenic strokes have intermittent AFIB. Thus, there is increased interest in recording transient episodes of AFIB which requires something other than the use of a diagnostic resting ECG device.

AFIB is not always persistent or chronic, and thus is often not present when a resting 12-lead ECG is obtained. The use of implantable devices to detect AFIB, has made it clear that transient episodes of AFIB are more common than first realized. In fact, detection rates exceeding 10% have been reported after cryptogenic stroke. In addition, AFIB often returns weeks or months after the source has been successfully ablated. Obviously, implantable recording devices have the advantage of enforced patient compliance. On the other hand, there is the added expense and the invasive procedure with possible complications that goes with it. This has prompted the development of easy-to-use long-term recording devices which typically rely on a single lead ECG. These include electrode patches that can be continuously worn for weeks of time or simple hand-held ECG devices that can be used by the patient to periodically (yet regularly) capture 30 seconds of a single lead ECG.

Independent Diagnostic Testing Facilities (IDTFs) are often challenged with receiving and processing the massive amounts of ECG data recorded by these ECG devices that monitor a patient for weeks or months at a time. IDTFs are tasked with viewing and editing thousands of ECG recordings per day. Furthermore, the amount of time and expertise necessary to evaluate each of these tracings is not the same. Some may require an expert and take minutes to evaluate; others, a few seconds. This is often due to the following factors: (1) poor signal quality and/or high levels of noise; (2) the duration of the arrhythmic event; and (3) the degree of complexity of the arrhythmic event. Due to these reasons, laboratory services often use manual methods to triage the reading of recordings to different staff members that have different skill sets. These manual methods require significant manpower and time, which raises the price of lab services and the delay in providing results.

Currently available systems and methods for automatic AFIB detection of continuous ECG data rely on a beat-by-beat analysis of the heart rhythm, such as the RR interval, to determine whether the rhythm meets certain variability requirements indicative of AFIB. An example of such a system is the EK-Pro®, by General Electric Company of Schenectady, NY. Requires a long recording, which is bad when some recordings are only 30 seconds long. Often not enough data and, under such constraints, cannot However, the inventors have recognized that such beat-by-beat detection algorithms are unreliable, especially when dealing with shorter data recordings (such as 30 second ECG recordings), because they often are unable to differentiate between AFIB and other benign arrhythmias, such as premature atrial contractions (PACs) and sinus arrhythmias (SAs), especially based on relatively short or non-consecutive sections of ECG data or in the presence of noise in the ECG recording.

Other systems and methods for detecting AFIB are for processing diagnostic 12-lead ECG data, which is generally a controlled and low noise ECG recording that is taken in a controlled environment by a trained professional. One such system is the Marquette 125L® ECG Analysis Program, by General Electric Company of Schenectady, NY. However, the inventors recognized that such algorithms configured for detecting AFIB in diagnostic 12-lead ECG data were not developed to be used on data recorded by long-term continuous ECG monitoring systems, which often only include one lead (or at most three leads) of data and operate in noisy environments as the patient moves and engages in daily activities. Such segment analysis modules generally require multiple leads and clean data in order to provide accurate AFIB detection because they rely on detection of P waves, which are relatively small in amplitude. Rather than looking for variability patterns, like the beat-to-beat algorithms, these diagnostic 12-lead processing algorithms look at segments of 12 lead data, such as 10 second segments, to identify patterns in those time segments of data that indicate other arrhythmias and rule out AFIB. Such algorithms, such as the 12SL®, rely on the detection on P-waves and other logic that can exclude the presence of AFIB. If no other arrhythmia type can be identified, then AFIB is detected as a last resort using a process of elimination.

The inventors have recognized the forgoing problems and challenges faced by IDTFs, and with current AFIB detection algorithms in general. Accordingly, the inventors recognized a need for a robust and reliable system and method for automatically detecting AFIB that can process any ECG data—e.g., regardless of signal source, lead arrangement or number of leads, sample frequency, data resolution, noise level, etc.—to facilitate AFIB detection. The disclosed system 1, an embodiment of which is illustrated in FIG. 1, and method 100 utilizes two different ECG processing methods in parallel to process the ECG data—(1) a beat module 12 that conducts a beat-by-beat analysis of a time series of ECG data to detect AFIB based on rhythm variability, such as variation in the RR interval; and (2) a segment module 14 that breaks the time series of ECG data into time segments of data, which may be overlapping time segments, and analyzes the time segments to determine whether AFIB is present or absent based on a whether a rhythm other than atrial fibrillation is detected—i.e., detecting AFIB by eliminating the probability of other rhythms and arrhythmia types. The results of the beat module 12 and the segment module 14 are then compared to generate an AFIB determination value indicating the presence or absence of AFIB in the relevant section of ECG data. If results of both approaches agree, namely the output of each of the beat module 12 and the segment module 14 provide the same determination regarding the presence or absence of AFIB, then the result is more likely to be correct.

FIG. 1 depicts one embodiment of a system 1 for processing ECG data. In the figure, an ECG monitor 5 records ECG data from a patient 3 via two electrodes 7 attached to the patient. Thus, one lead of ECG data is recorded, which may be recorded over a very long period of time, such as days, weeks, or months. As described above, the ECG data may be recorded in intervals, such as intervals of thirty seconds or as long as several minutes. Alternatively, the ECG monitor 5 may be configured to continually record ECG data from the patient. The ECG data 10 is then transmitted or transferred to the system 1 for storage and processing. For example, the ECG data 10 from the patient 3, as well as from several other patients, may be stored in a database 11 of ECG data awaiting processing for detection of AFIB and/or other arrhythmias. To begin processing the ECG data 10 recorded from the patient 3, a time series of the ECG data is provided to both the beat module 12 and the segment module 14. For example, the entirety of the ECG data 10 may be provided, in a time series fashion according to its time of recording, to each of the beat module 12 and the segment module 14. The time series of ECG data is thus processed by both modules, which utilize differing analysis methods to determine whether AFIB is present throughout the time series of ECG data.

The beat module 12 determines a beat AFIB value 36 based on a timing of each identified heartbeat in the time series of ECG data 10 (see FIG. 4), wherein the beat AFIB value 36 represents a presence or absence of AFIB based on variability in the timing of each identified heartbeat. In one embodiment, the beat AFIB module 12 utilizes a Hidden Markov Model (HMM) to continually process the time series of ECG data and statistically assess whether AFIB is present. In one embodiment, the HMM is configured to represent the RR intervals, such as with respect to a sliding average RR interval, in one of two states: chaotic or organized, or AFIB or NO AFIB, respectively. For example, the HMM may be trained using a database of ECG data selected to contain AFIB, normal sinus rhythm, and other rhythms considered likely to be confused with AFIB. For each beat, the current score of HMM value is updated. Then a buffer containing previous history of HMM score is also updated. The average HMM score is calculated for every updating cycle, which is the beat AFIB value 36. The timing of the beat AFIB value 36 calculation may correspond with the output of the segment module 14 so that the values can be accurately compared to determine the AFIB identification value 40. For example, the beat AFIB value 36 may be outputted every five seconds, and the segment module 14 may analyze time segments that shift by five seconds, such as overlapping time segments having a start time that shifts by five seconds.

In one embodiment, the segment module 14 is operated to perform a running mode analysis of overlapping segments of the ECG data 10 to produce a segment AFIB value 38 for each overlapping segment of the ECG data 10. For example, the segment module 14 may comprise software instructions executable to identify whether any rhythm from a set of known rhythms, which may include various arrhythmia patterns, are likely to be present in the time segment of ECG data 10, in which case it would rule out the presence of AFIB. To provide just a few examples, the set of known rhythms (which include known arrhythmia patterns) may include any one or more of the following: the presence of P-waves, artificial pacing, ectopic atrial rhythm, atrial flutter, junctional rhythm, or PACs. For example, if the presence of P waves or PACs are detected, then the presence of AFIB in the time segment may be ruled out.

The segment module 14 divides the time series of ECG data 10 into consecutive time segments, which may be overlapping time segments. The ECG data in each of the time segments has been analyzed to determine a segment AFIB value 38 for that time segment, wherein the segment AFIB value 38 indicates a presence or absence of AFIB in the time segment based on whether any of the set of known rhythms are identified. For example, the time segments may be ten second segments of the ECG data 10. In one embodiment, the segment module 14 may overlap the time segments such that each sample in the ECG data 10 is analyzed as part of at least two time segments. For example, the segment module 14 may be configured to shift the time segments in five second increments. In an embodiment where the time segments are ten seconds long, each data point, or sample, will be analyzed as part of two time segments. This provides a robust data analysis.

The time series of ECG data 10 may comprise 12 leads of data, and as such the segment module 14 may be configured to process 12 leads of data. However, as is common with long-term ECG monitoring, the time series of ECG data 10 may comprise fewer than 12 leads, such as five leads, three leads, or just one lead of data. Thus, for applications where the time series of ECG data comprises less than 12 leads of data, the available leads may be repeated in order to emulate 12 leads of data being supplied to the segment module 14. Thus, a single available lead may be repeated 12 times and supplied to the segment module as 12 leads of data. Where three leads are available, the leads may each be repeated four times, and so on.

In certain embodiments, the AFIB detection methods and logic executed by the segment module 14 may have some hysteresis effect where once a normal sinus rhythm (NSR) is detected the segment AFIB value 38 may rule out the presence of AFIB for a number of time segments. For example, as seen in FIG. 2, once a normal sinus rhythm is detected the segment AFIB value 38 remains at 0 for two five second intervals following detection of the normal sinus rhythm. Thus, once a normal sinus rhythm is detected, it takes a few analysis intervals for the segment AFIB value 38 to flip back to AFIB as the running answer.

The system 1 further includes an AFIB detection module 16 that determines an AFIB identification value 40 based on the beat AFIB value 36 and the segment AFIB value 38. If both the beat AFIB value 36 and the segment AFIB value 38 indicate the presence of AFIB, then the AFIB identification value 40 will also indicate the presence of AFIB. If the beat AFIB value 36 and the segment AFIB value 38 both indicate an absence of AFIB, then the AFIB identification value 40 will indicate an absence of the case situation where the beat AFIB value 36 and the segment AFIB value 38 do not agree. In certain embodiments, the AFIB detection module 36 may be operable in various modes to execute differing logic for handling disagreements between the beat AFIB value 36 and the segment AFIB value 38. For example, the AFIB detection module may be configured to operate in one of three modes, including a high sensitivity mode, a high specificity mode, and a balanced mode to determine the AFIB identification value 40 based on the beat AFIB value 36 and the segment AFIB value 38.

FIG. 2 depicts an exemplary embodiment of the logic executed in three different modes to determine the AFIB identification value 40. In the explanatory example, each of the beat module 12 and the segment module 14 output respective values indicating the presence or absence of AFIB (either a 1 or a 0, respectively) for every five second increment of ECG data 10. The example shows five such values; however, it should be understood that the values will continue for the length of the time sequence of ECG data 10.

In the example, the AFIB detection module 16 can operate in the high sensitivity mode where the AFIB identification value 40 indicates a presence of AFIB when either the beat AFIB value 36 or the segment AFIB value 38 indicates the presence of AFIB. Thus, in high sensitivity mode, an OR Boolean operator is used to compare the beat AFIB value 36 and the segment AFIB value 38. Further, in high sensitivity mode the threshold for the HMM to recognize an organized RR pattern may be increased. This increases the chance that the beat module 12 will detect that the ECG data 10 is chaotic and generate a beat AFIB value 36 indicating the presence of AFIB, thus increasing the sensitivity of the AFIB detection by the beat module 12. Alternatively, the AFIB detection module 16 may operate in a high specificity mode where the AFIB identification value 40 indicates a presence of AFIB when both of the beat AFIB value 36 and the segment AFIB value 38 indicate the presence of AFIB. Thus, in high specificity mode an AND Boolean operator is used to compare the beat AFIB value 36 with the segment AFIB value 38. The AFIB detection module 16 may be further operable in a balanced mode where the AFIB identification value 40 indicates a presence of AFIB when either the beat AFIB value or the segment AFIB value indicates the presence of AFIB. In certain embodiments, the beat module 12 has a lower threshold for detecting the presence of AFIB in the high sensitivity mode than in the balanced mode, thus the sensitivity of the detection algorithm will be greater in the sensitivity mode than in the balanced mode.

In certain embodiments, the operating mode may be selected by a user. For example, the user may select one of the high sensitivity mode, the high specificity mode, or the balanced mode via the user interface 22 associated with the system 1.

In certain embodiments, a confidence level (CL) may be calculated for each AFIB identification value 40. For example, the confidence level may be a running value accounting for all AFIB identification values 40 determined for the time series of ECG data 10. For example, the confidence level (CL) may be determined as the total number of AFIB detection values 40 indicating the presence of AFIB (e.g., equal to 1) divided by the total number of AFIB identification values 40 overall. The confidence level may be expressed as a percentage—e.g., the percent of AFIB identification values 40 indicating the presence of AFIB. Thus, depending on the mode being executed by the AFIB detection module 16, the confidence level may vary. Referring to the example of FIG. 2, CL would equal 100% for the first time segment, 50% for the second time segment, and CL would vary for the remaining time segments depending on the mode of operation executed by the AFIB detection module 16.

In certain embodiments, the confidence level may also account for a noise level 39 of the respective segment of ECG data analyzed. The noise level may be assessed by logic incorporated in either the beat module 12, the segment module 14, or by a separate noise analytic module. In the depicted embodiment, the segment module 14 measures the noise level 39 in the analyzed segment of the time series of ECG data 10 and generates a positive value if the noise exceeds a noise threshold and a negative value (or a 0) if the noise level does not exceed the noise threshold. In other embodiments, the noise level 39 may be placed on a noise scale, or may otherwise by indicated by using more than two values. The confidence level 41 may then be decreased when significant noise is present in the time segment. For example, when the noise level 39 exceeds a noise level threshold, the confidence level 41 may be reduced by a predetermined amount. In the depicted example, the noise level 39 determined by the segment module 14 exceeds the noise level threshold for one time segment, and the confidence level (CL) 41 is reduced by 20% by the AFIB detection module 16 for the corresponding time segment. In other embodiments where the noise level 39 determination may include more than two values, the confidence level 41 may be reduced by an increasing percentage amount for increasing noise levels.

Figure 3:
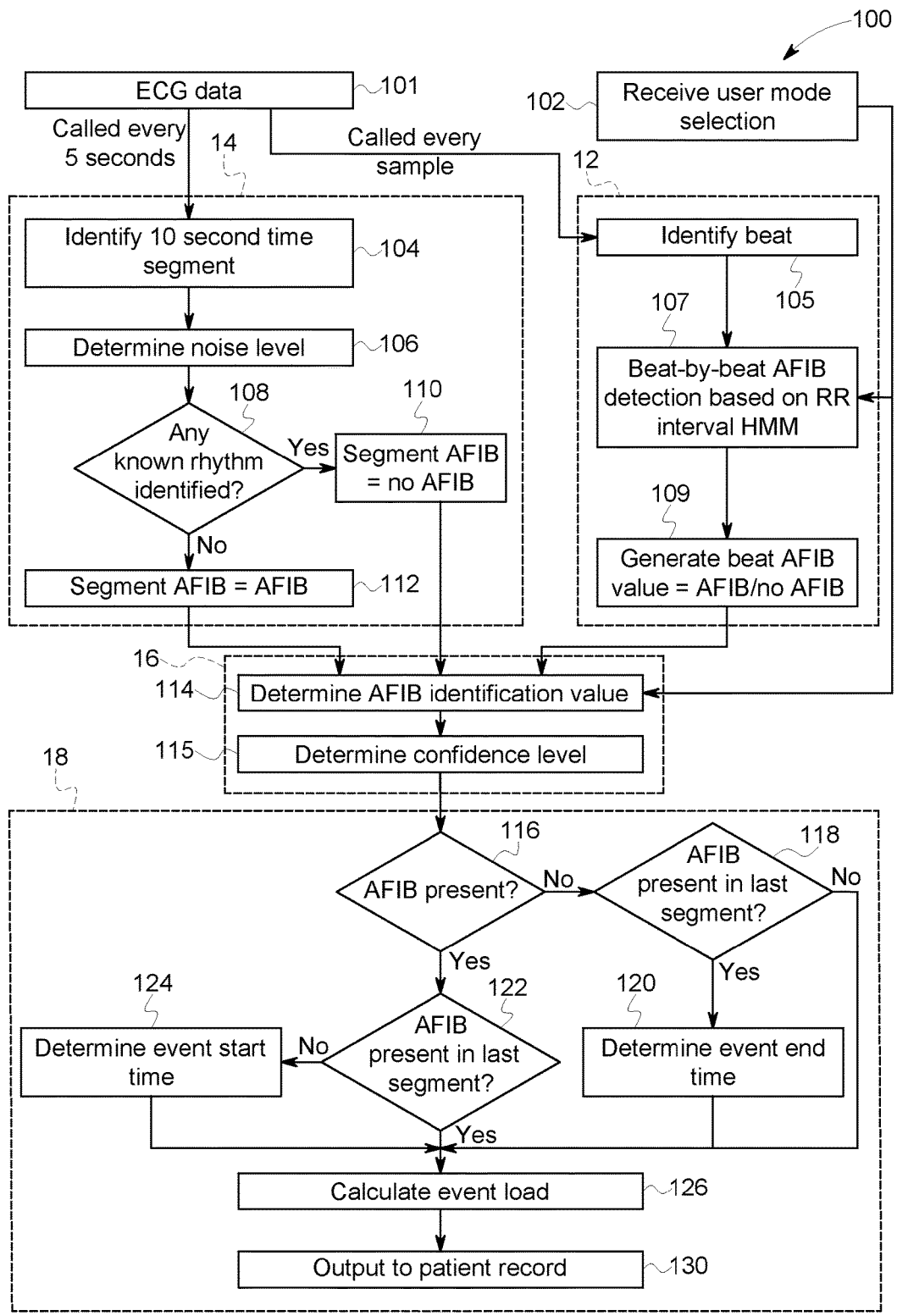
FIG. 3 is a flowchart representing one embodiment of a method of processing ECG data to detect atrial fibrillation.

FIG. 3 depicts one embodiment of a method 100 of processing ECG data to detect atrial fibrillation. The sample points of the ECG data are continually received at step 101 and processed in parallel by the beat module 12 and segment module 14. With respect to the beat module 12, instructions are executed to analyze the ECG data 10 on a sample-by-sample basis to identify beats at step 105 within the ECG data 10. Upon identification of a beat, the HMM determines at step 107 whether the beats represents a chaotic or an organized RR interval, which is a determination made based on all of the ECG data 10 processed thus far by the beat module 12. The threshold used by the HMM for determining whether the beat data is organized or chaotic may be adjusted based on the mode selection 30 by a user, which is received at step 102. As described above, the mode selection 30 may adjust the sensitivity of the AFIB detection by the HMM. The state of the HMM AFIB determination is polled at a regular interval, such as every five seconds, to generate the beat AFIB value 36 at step 109. The period at which the beat AFIB value 36 is polled, or generated, may be shorter or longer than five seconds, as it may correspond to the length of the segments, or segment shifts, executed by the segment module 14.

The segment module 14 operates on the ECG data 10 in parallel with beat module 12. The segment module 14 calls the ECG data 10 in time segments. In the depicted embodiment, the segment module 14 calls new data every five seconds and analyzes a shifting ten second time segment, identified at step 104. The noise level 39 of the ECG data in the time segment is determined at step 106. For example, the signal-to-noise ratio may be determined and classified, such as by comparing it to one or more noise level thresholds. Instructions are executed at step 108 to determine whether any known rhythm can be identified, such as the presence of a P wave, a normal sinus rhythm (NSR), artificial pacing, ectopic atrial rhythm, atrial flutter, junctional rhythm, or premature atrial contractions (PACs). If any such known rhythm is identified, then at step 110 the segment module 14 determines that AFIB is not present and assigns the segment AFIB value 38 to indicate no AFIB (such as equaling 0). If no known rhythm is identified, then the presence of AFIB is positively determined for the time segment and the segment AFIB value is set at step 112 to indicate the presence of AFIB (such as equaling 1). Logic is then executed at step 114, such as by executing code embodied in the AFIB detection module 16, to determine the AFIB identification value 40 based on the beat AFIB value 36 and segment AFIB value 38. The AFIB detection module 16 may execute varying logic depending on the user mode selection 30 received at step 102, such as whether the system is operating in high sensitivity mode, high specificity mode, or balanced mode. The AFIB detection module 16 may further determine the confidence level 41 for the respective time segment, which may be a running value based on all previous AFIB identification values 40 for the time series of ECG. In other embodiments, the confidence level 41 may be determined at a different stage, and instructions for such calculation may be embodied in a different module, such as in the AFIB analysis module 18 or as a stand alone software module called at some point during the steps represented as the segment module 16 and the AFIB analysis module 18.

The output of the AFIB detection module 16 over time may be analyzed by an AFIB analysis module 18, such as to present information aggregating the AFIB identification values 40 for the time series of ECG data 10. For example, the AFIB analysis module 18 may analyze the identification values 40 to identify continuous AFIB events within the time series of ECG data 10 and calculate an event load 44. In certain embodiments, the AFIB analysis module 18 may be called once all of the AFIB identification values 40 have been determined for the time series of ECG data 10. In other embodiments, like that depicted in FIG. 3, the instructions of the AFIB analysis module 18 may be executed on a running basis as AFIB identification values 40 are generated by the AFIB detection module 16. If a received AFIB identification value 40 indicates that AFIB is not present, as determined at step 115, then logic is executed to determine whether AFIB was present in the last segment, which is represented at box 118. If AFIB was present in the last time segment, but is not currently present, then an AFIB event has ended, and an event end time is determined at step 120 for the AFIB event. If the received AFIB identification value 40 did indicate the presence of AFIB, as determined at step 116, then logic is executed at step 122 to determine whether AFIB was present in the last segment. If AFIB was not previously present, but now is, then an event start time is determined at step 124. If AFIB was present in the last segment and continues to be present, then the AFIB event continues through the current segment. A running event load value 44 may be calculated at step 126 based on the available event start times and end time. For example, the event load 44 may represent a total percent of time segments processed thus far where AFIB was detected, thus representing the percentage of the time series of ECG data 10 where AFIB is determined to be present. Alternatively or additionally, the event load may account for a number of separate AFIB events (each having a start and an end time), and thus may indicate whether AFIB was continuously detected for long periods or whether it was detected in short bursts, separated by intermittent detection of organized and/or known rhythms.

The values determined and calculated by the module(s) 12, 14, 16, 18 may then be stored in the patient record 130, such as in the patient record database 20, to be accessed at a later date by a clinician caring for the patient 3. In certain embodiments, the AFIB identification values 40, confidence values 41, and/or the event load value 44 may be displayed, such as on a display associated with the user interface 22 of the system 1. Alternatively or additionally, the processed data may be stored in the ECG data database 11, which may then be accessed by a clinician and/or moved to the patient record database 20 at a later date and/or as part of separate process.

Figure 4:
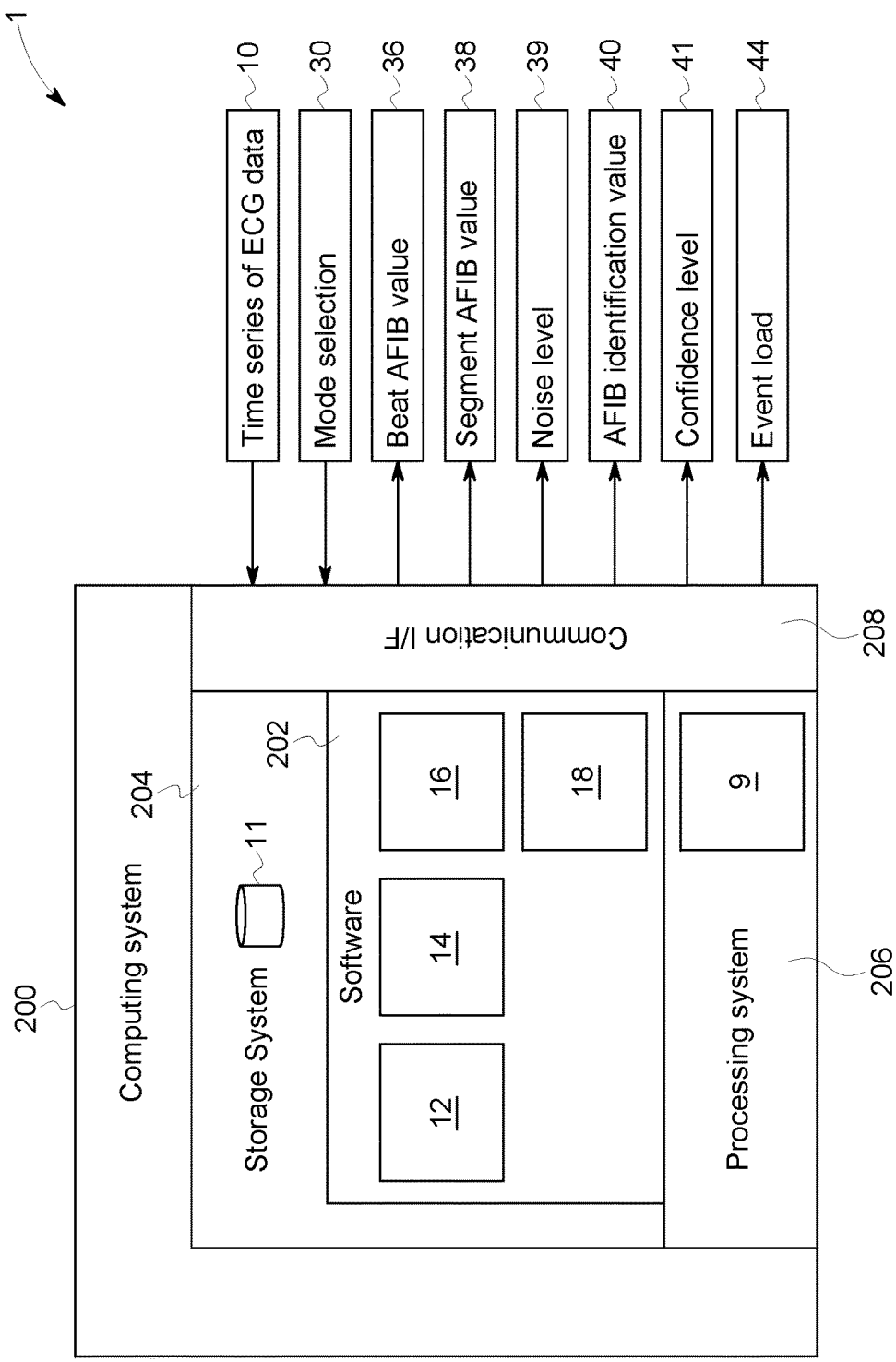
FIG. 4 is a schematic diagram of a computing system that may be incorporated in one embodiment of a system for processing ECG data to detect atrial fibrillation.

FIG. 4 provides another system diagram of an exemplary embodiment of the system 1 for analyzing ECG data having a beat module 12, a segment module 14, an AFIB detection module 16, and an AFIB analysis module 18. The system 1 is generally a computing system 200 that includes a processing system 206, storage system 204, software 202, and communication interface 208. The processing system 206 loads and executes software 202 from the storage system 204, including the beat module 12, the segment module 14, the AFIB detection module 16, and the AFIB analysis module 18, which are applications within the software 202. Each of the modules 12, 14, 16, 18 includes computer-readable instructions that, when executed by the computing system 200 (including the processing system 206), direct the processing system 206 to operate as described in herein in further detail.

Although the computing system 200 as depicted in FIG. 4 includes one software 202 encapsulating one beat module 12, one segment module 14, one AFIB detection module 16, and one AFIB analysis module 18, it should be understood that one or more software elements having one or more modules may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes the processor 9, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204, which includes the ECG database 11 and may also include the patient records database 20, can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. For example, the software 202 may be stored on a separate storage device than the ECG database 11. Likewise, ECG database 11 can be stored, distributed, and/or implemented across one or more storage media or group of storage medias. Similarly, ECG database 11 and/or the patient records database 20 may encompass multiple different sub-databases at different storage locations and/or containing different information which may be stored in different formats. Storage system 204 can further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as the user interface 22 and/or the ECG monitor 5.

The user interface 222 is configured to receive input from a clinician, including the mode selection input 30 selecting one of the high sensitivity mode, the high specificity mode, and the balanced mode. User interface 22 may include a mouse, a keyboard, a voice input device, a touch input device (such as a touch screen) for receiving a touch gesture from a user, a motion input device for detecting non-touch gestures and other motions by a user, and other comparable input devices and associated processing elements capable of receiving input from a user, such as a clinician. Output devices such as a video display or graphical display can display an interface further associated with embodiments of the system and method as disclosed herein. Speakers, printers, haptic devices and other types of output devices may also be included in the user interface 22.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A system for processing ECG data to detect atrial fibrillation (AFIB), the system comprising:
    a beat module comprising instructions stored on non-transitory storage media and executed to:
        receive a time series of ECG data;
        identify heart beats in the time series of ECG data;
        determine a beat AFIB value based on a timing of each identified heart beat, wherein the beat AFIB value represents a presence or absence of AFIB based on variability in the timing of each identified heart beat;
    a segment module comprising instructions stored on non-transitory storage media and executed to:
        receive the time series of ECG data;
        divide the time series of ECG data into two or more time segments;
        determine a segment AFIB value for each time segment, wherein the segment AFIB value indicates a presence or absence of AFIB in the time segment based on whether any of a set of known rhythms are identified;
    an AFIB detection module comprising instructions stored on non-transitory storage media and executed to determine an AFIB identification value for each time segment based on a combination of the beat AFIB value during that time segment and the segment AFIB value for that time segment.

2. The system of claim 1, wherein the two or more time segments are overlapping segments of the time series of ECG data.

3. The system of claim 2, wherein the two or more time segments each contain 10 seconds of the time series of ECG data, and consecutive time segments overlap by 5 seconds;
wherein the beat module implements Hidden Markov Model analysis based on RR intervals between each identified heart beat to generate a beat AFIB value every 5 seconds; and
wherein the AFIB identification value is determined every 5 seconds based on the most recent beat AFIB value and the most recent segment AFIB value.

4. The system of claim 3, wherein the AFIB detection module is configured to operate in any one of a high sensitivity mode, a high specificity mode, and a balanced mode to determine the AFIB identification value, wherein:
in high sensitivity mode the AFIB identification value indicates a presence of AFIB when either the beat AFIB value indicates the presence of AFIB or the segment AFIB value indicates the presence of AFIB;
in high specificity mode the AFIB identification value indicates a presence of AFIB when both the beat AFIB value indicates the presence of AFIB and the segment AFIB value indicates the presence of AFIB;
in balanced mode the AFIB identification value indicates a presence of AFIB when either the beat AFIB value indicates the presence of AFIB or the segment AFIB value indicates the presence of AFIB; and
wherein the beat module has a lower threshold for detecting the presence of AFIB by the Hidden Markov Model analysis in the high sensitivity mode than in the balanced mode.

5. The system of claim 4, wherein the segment module is further executed to determine a noise level for the time segment; and
wherein the AFIB detection module, operating in at least one of the high sensitivity mode, the high specificity mode, and the balanced mode, further determines the AFIB identification value based on the noise level for the segment.

6. The system of claim 4, wherein operation of the AFIB detection module in one of the high sensitivity mode, the high specificity mode, and the balanced mode is based on a mode selection from a user input device.

7. The system of claim 1, further comprising an AFIB analysis module comprising instructions stored on non-transitory storage media and executed to:
detect an AFIB event based on the AFIB identification value for one or more sequential time segments in the time series of ECG data, wherein the AFIB event has a start time and an end time;
wherein the start time of the AFIB event is equal to a start time of a first time segment in a series of consecutive time segments where AFIB is detected, and an end time for the AFIB event is equal to an end time of a last time segment in a series of consecutive time segments where AFIB is detected; and
wherein the AFIB analysis module is further executed to calculate an event load for the time series of ECG data based on all AFIB events in the time series of ECG data, and the start time and end time of each AFIB event.

8. The system of claim 1, wherein the segment module is further executed to determine the segment AFIB value is based on 12 leads of ECG data for the time segment.

9. The system of claim 8, further comprising an ECG monitor collecting one lead of ECG data from a patient, wherein the time series of ECG data comprises only the one lead of ECG data; and
wherein each segment of the time series of ECG data is repeated 12 times to emulate 12 leads of data provided to the segment module to determine the segment AFIB value.

10. The system of claim 1, wherein the set of known rhythms includes at least one of a presence of P-wave, artificial pacing, ectopic atrial rhythm, atrial flutter, junctional rhythm, and premature atrial contractions; and
wherein the segment module determines that the segment AFIB value equals an absence of AFIB in the time segment when any of the set of known rhythms are identified in the time segment, and determines that the segment AFIB value equals a presence of AFIB when none of the set of known rhythms are identified in the time segment.

11. The system of claim 1, wherein the AFIB detection module is configured to operate in either one of at least a high sensitivity mode and a high specificity mode to determine the AFIB identification value;
wherein in high sensitivity mode the AFIB identification value indicates a presence of AFIB when either the beat AFIB value indicates the presence of AFIB or the segment AFIB value indicates the presence of AFIB, and in high specificity mode the AFIB identification value indicates a presence of AFIB when both the beat AFIB value indicates the presence of AFIB and the segment AFIB value indicates the presence of AFIB.

12. A computer-implemented method of processing ECG data to detect atrial fibrillation (AFIB), the method comprising:
receiving a time series of ECG data;
identifying each heart beat within the time series of ECG data;
determining a beat AFIB value based on a timing of each identified heart beat, wherein the beat AFIB value represents a presence or absence of AFIB based on variability in the timing of each identified heart beat;
dividing the time series of ECG data into two or more time segments;
determining a segment AFIB value for each time segment, wherein the segment AFIB value indicates a presence or absence of AFIB in the time segment ECG data based on whether any of a set of known rhythms are identified; and
determining an AFIB identification value for each time segment based on a combination of the beat AFIB value during that time segment and the segment AFIB value for that time segment.

13. The method of claim 12, receiving a user mode selection for determining the AFIB identification value, wherein the user mode selection is one of a high sensitivity mode, a high specificity mode, or a balanced mode; and
wherein the AFIB identification value is determined according to the user mode selection.

14. The method of claim 13, wherein:
in high sensitivity mode the AFIB identification value indicates a presence of AFIB when either the beat AFIB value indicates the presence of AFIB or the segment AFIB value indicates the presence of AFIB;
in high specificity mode the AFIB identification value indicates a presence of AFIB when both the beat AFIB value indicates the presence of AFIB and the segment AFIB value indicates the presence of AFIB;

in balanced mode the AFIB identification value indicates a presence of AFIB when either the beat AFIB value indicates the presence of AFIB or the segment AFIB value indicates the presence of AFIB; and wherein the beat module has a lower threshold for detecting the presence of AFIB by a Hidden Markov Model analysis in the high sensitivity mode than in the balanced mode.

15. The method of claim 12, wherein the two or more time segments are overlapping segments of the time series of ECG data.

16. The method of claim 15, wherein the two or more time segments each contain 10 seconds of the time series of ECG data, and consecutive time segments overlap by 5 seconds.

17. The method of claim 16, wherein the step of determining the beat AFIB value includes implementing a Hidden Markov Model analysis based on RR intervals between each identified heart beat to generate a beat AFIB value every 5 seconds;

wherein the AFIB identification value is determined every 5 seconds based on the most recent beat AFIB value and the most recent segment AFIB value.

18. The method of claim 12, wherein the time series of ECG data comprises 12 leads of ECG data, and wherein the segment AFIB value is based all 12 leads of ECG data in the time segment.

19. The method of claim 12, wherein the time series of ECG data comprises only one lead of ECG data, and further comprising processing each segment of the time series of ECG data 12 times to determine the segment AFIB value.

* * * * *